United States Patent [19]

DeFrank

[11] Patent Number: 5,242,432
[45] Date of Patent: Sep. 7, 1993

[54] NEEDLELESS ADAPTER

[75] Inventor: Michael P. DeFrank, Temecula, Calif.

[73] Assignee: IVAC, San Diego, Calif.

[21] Appl. No.: 766,603

[22] Filed: Sep. 26, 1991

[51] Int. Cl.⁵ .......................................... A61M 25/00
[52] U.S. Cl. .................... 604/284; 604/247; 604/83
[58] Field of Search ............... 604/9, 122, 249, 256, 604/283, 284, 83, 27, 86, 87, 247; 251/149.6, 337, 347; 137/540, 543.17, 547

[56] References Cited

U.S. PATENT DOCUMENTS

| | | | |
|---|---|---|---|
| 2,594,405 | 4/1952 | Deters | 251/337 |
| 2,899,975 | 8/1959 | Fernandez | 137/543.17 |
| 2,999,499 | 9/1961 | Willet | 604/83 |
| 3,416,567 | 12/1968 | Von Dardel et al. | 604/83 |
| 3,994,293 | 11/1976 | Ferro | 604/83 |
| 4,387,879 | 6/1983 | Tauschinski | 604/249 |
| 5,041,087 | 8/1991 | Loo et al. | 604/83 |
| 5,049,128 | 9/1991 | Duquette | 604/249 |

Primary Examiner—C. Fred Rosenbaum
Assistant Examiner—Manuel Mendez

[57] ABSTRACT

A medical valve assembly comprises a valve body having a fluid passage therethrough, a valve member, and an urging means disposed within the fluid passage. The valve member is adapted to seal against a sealing surface of the fluid passage and the urging means is adapted to urge the valve member against the sealing surface. The medical valve can be used without a needle thereby eliminating risks associated with needle stick injuries. In applications where it is expedient to use a needle (such as prepackage medications) the medical valve accommodates the use of a needle to administer medication. The urging means is disclosed in a first embodiment wherein it is formed integral with the head portion of the valve member. In an alternative embodiment, the urging means is separate from the head portion of the valve member and is comprised of a metallic spring element.

8 Claims, 2 Drawing Sheets

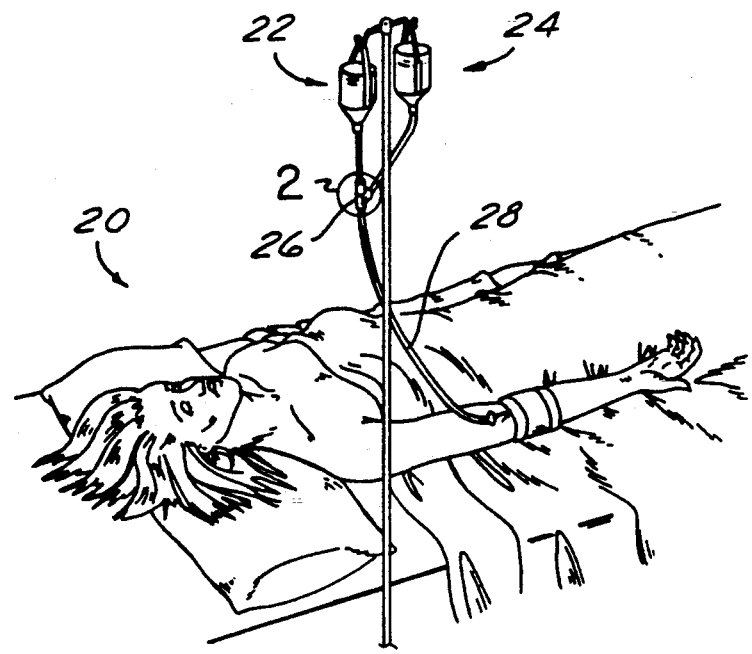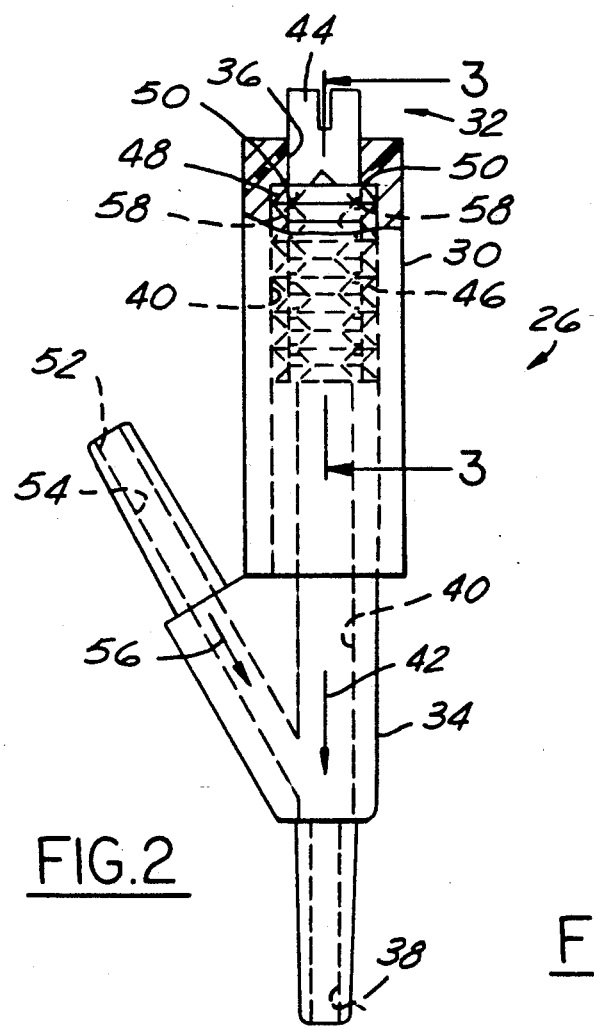

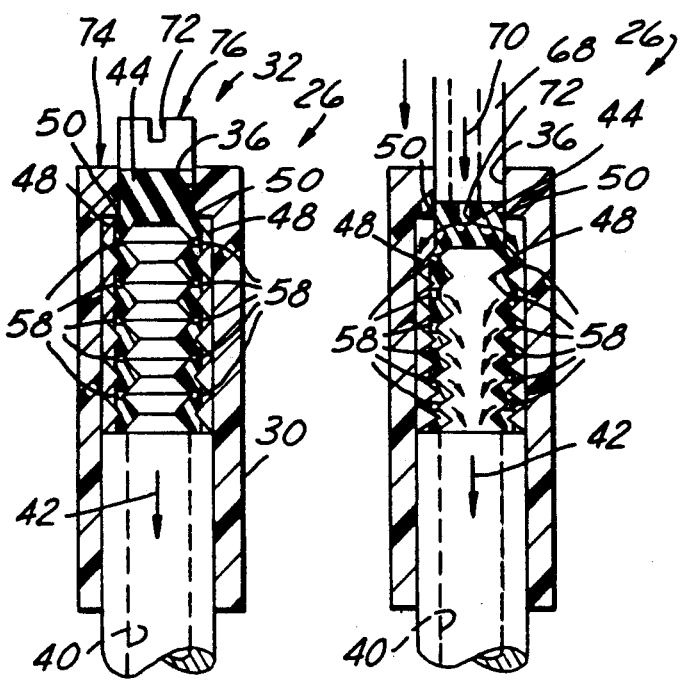

NEEDLELESS ADAPTER

BACKGROUND OF THE INVENTION

The present invention relates generally to connectors and more specifically relates to connectors for use in introducing medication into a patient and for removing fluids from the patient.

Modern medical practice commonly employs intravenous (I.V.) solutions to administer medications to patients. In most such applications, an intravenous solution flows from an elevated container through tubing which is connected to a needle inserted directly into the patient's vein. Intermittent or "piggy-back" medications are typically added to the intravenous solution at a connector placed in the tubing known as a "Y-site" connector. Y-site connectors generally include a sealed entry port which is integral to the tubing through which fluid flows to (or from) the patient. The sealed entry port of a Y-site connector is typically constructed from a latex plug (generally known as a septum). Medication is introduced into the tubing by penetrating the septum with a secondary needle connected to a syringe or other source of medication. The latex septum is advantageous in that it allows for multiple needle insertions to access a patient's system with no pain or discomfort to the patient. The latex septum is self-healing, and upon removal of the needle the hole through the septum closes thus maintaining a closed system. The self-healing feature of the latex septum as well as its flat surface serve as distinct advantages inasmuch as before and after each needle insertion, the exterior surface of the septum can be easily wiped down with alcohol to disinfect the surface and minimize the introduction of bacteria and infection to the patient.

One major drawback with the above-referenced conventional practice is that, in addition to the primary needle used to puncture the patient's vein, it necessitates the use of a secondary needle to puncture the septum. Once this secondary needle is exposed to a patient's body fluids it is considered high risk and threatens the health of healthcare workers. Used needles must be handled and disposed of very carefully and the mishandling of used needles accounts for a large percentage of life-threatening injuries to medical personnel.

Several devices have been developed for providing secondary access to a patient's bloodstream without the use of a needle. For example, U.S. Pat. No. 3,570,484 issued to Steer, et al. discloses a device for administering intravenous injections of liquid. U.S. Pat. No. 4,324,239 issued to Gordon, et al. relates to a safety valve for catheterization and is characterized by a piston having an internal flow path. A portion of the piston is surrounded by an elastomeric member which biases the piston in a closed position. Although the above-referenced devices do eliminate the secondary needle connection, and therefore eliminate the risk of needle stick injury to medical personnel, they both present designs which present an unnecessary risk of infection to the patient. This risk is primarily due to the devices are designed with external crevices which promote the pooling of fluid on and around the external surfaces of the device. This pooling effect creates a fluid reservoir during the normal course of using the device. Ideally, a device connected to a patient's bloodstream should not promote pooling during the normal course of its use due to the potential for bacterial infection. If the fluid reservoir or cavity is not clean, bacteria may develop in the reservoir. That bacteria could find its way into a patient's bloodstream when the device is used to administer new medication or to remove fluids from the patient's bloodstream.

While, as discussed above, in most applications it is desirable to eliminate the needle in secondary connections, it is generally accepted that in some applications the use of a needle to make the secondary connection is expedient. For example, certain medications are commonly prepackaged in needle assemblies. When using prepackaged medications, it is understood that it is desirable to simply insert the needle through the latex septum of the Y-site connector and dispose the medication into the I.V. solution.

It is desirable that such a needleless connector be inexpensive to manufacture, disposable, and easily adaptable for use in various medical applications.

Thus it is an object of this invention to eliminate the necessity of using a secondary needle as a component in tubing connections related to intravenous delivery of medication while still providing for the use of a needle in circumstances where expedient, such as in the case of medication which is prepackaged in needle assemblies.

It is a further object of this invention to provide a Y-site connector which is easily connectable to a syringe, I.V. administration sets, or other standard medical fittings.

It is still a further object of this invention to provide a Y-site connector which is extremely simple in design, inexpensive to produce, and easy to disinfect.

BRIEF DESCRIPTION OF THE INVENTION

A primary object of the present invention is to provide a medical valve assembly which allows intravenous access to a patient for the infusion or aspiration of fluids. To accomplish this the medical valve assembly includes a valve body having first and second openings and a first internal wall which joins the first and second openings. The first internal wall forms a first fluid passage for communicating a first fluid between the first and second opening. The first internal wall includes a seating surface. A valve member is disposed in and moves within the first fluid passage and is adapted to contact the seating surface thereby preventing the first fluid from communicating between the first and second openings through the first fluid passage. A spring or similar urging means is disposed in the first fluid passage for urging the valve member against the seating surface. When a force of sufficient strength is exerted against the valve member, the valve member is urged from the seating surface thereby permitting the first fluid to communicate between the first and second openings through the first fluid passage.

The valve member is preferably comprised of puncturable material so that it may be penetrated by a hypodermic needle or the like. The valve member and the urging means are preferably integrally formed as one piece so as to reduce manufacturing costs. An alignment rail is preferably disposed on the internal wall of the first fluid passage and an alignment slot is preferably placed in the urging means. The alignment slot and the alignment rail are both adapted to cooperatively engage one another thereby guiding the movement of the valve member and maintaining the valve member in a fixed orientation within the first fluid passage. The alignment slot and the alignment rail act to prevent the valve member from jamming or cocking within the first fluid passage.

The valve assembly preferably includes a third opening and a second internal wall wherein the second internal wall joins the third opening to the first fluid passage. The second internal wall forms a second fluid passage for communicating a second fluid between the third opening and the first fluid passage.

The spring, or other urging means, preferably includes a generally tubular body having holes therethrough. The holes form a passage for the first fluid as it travels from the first opening to the second opening.

BRIEF DESCRIPTION OF THE DRAWINGS

FIG. 1 is an isometric view of a patient being administered medication intravenously using the Y-site connector of the present invention.

FIG. 2 is an enlarged cross-sectional view of the Y-site connector located within encircled portion 2 of FIG. 1.

FIG. 3 is a partial cross-sectional view of the Y-site connector of the present invention taken substantially along lines 3—3 of FIG. 2.

FIG. 4 is a partial cross-sectional view of the Y-site connector of the present invention taken substantially along lines 4—4 of FIG. 3.

FIG. 5 is a partial cross-sectional view of the Y-site connector of the present invention depicted in its close position.

FIG. 6 is a partial cross-sectional view of the Y-site connector of the present invention shown in its open position.

FIG. 7 is a top view of the retaining cap portion of the Y-site connector of the present invention.

FIG. 8 is a cross-sectional view of the retaining cap portion of the Y-site connector of the present invention taken substantially along lines 8—8 of FIG. 7.

FIG. 9 is a top view of the valve member portion of the Y-site connector of the present invention.

FIG. 10 is a cross-sectional view of the valve member portion of the Y-site connector of the present invention taken substantially along lines 10—10 of FIG. 9.

FIG. 11 is a partial phantom view of the Y-site connector of the present invention having its valve member punctured by a hypodermic needle.

FIG. 12 is an alternative embodiment of the valve member of the present invention.

DETAILED DESCRIPTION OF THE PREFERRED EMBODIMENTS

Now referring to FIG. 1, patient 20 is shown being administered intravenous (I.V.) fluid. This intravenous fluid is comprised of two solutions. The first solution, housed in container 24, is generally known as an intravenous solution (also called a parenteral liquid). The second solution is housed in container 22 and is generally known as "piggy-back" medication. These two solutions are combined at Y-site connector 26 and flow through tube 28 into a vein of patient 20. Although Y-site connector 26 is typically used for administering secondary medications, it is not limited to this application but can be used in any instance where a fluid must be introduced into, or extracted from, an existing fluid flow path.

Now referring to FIG. 2, Y-site connector 26 is comprised of three components—retaining cap 30, valve member 32 and base 34. Retaining cap 30 includes first entrance opening 36 and base 34 includes exit opening 38. Internal wall 40 joins first entrance opening 36 and exit opening 38 forming fluid passage 42 for communicating fluid between opening 36 and opening 38. Valve member 32 is disposed within fluid passage 42 and includes head portion 44 and biasing portion 46. Head portion 44 includes an outwardly extending shoulder 48 which is adapted to engage sealing surface 50 of retaining cap 30. The contact between sealing surface 50 and shoulder 48 prevents fluid flow through fluid passage 42 when valve member 32 is in the position depicted in FIG. 2. Thus, it is seen that the Y-site connector of FIG. 2 is adapted to prevent fluid flow from first entrance opening 36 to exit opening 38 through fluid passage 42. Second entrance opening 52 is connected to fluid passage 42 by way of internal wall 54. Internal wall 54 forms a second fluid passage 56 through Y-site connector 26.

Now referring to FIGS. 2, 3, and 4, head portion 44 and biasing portion 46 are preferably fabricated from a single piece of rubber, latex, thermoplastic rubber or the like. Biasing portion 46 includes bypass openings 58 disposed along opposing sides of biasing portion 46. Bypass openings 58 provide a path for fluid flow from first entrance opening 36 to exit opening 38 when Y-site connector 26 is in the open position. The open and close function of Y-site connector 26 will be discussed in detail in conjunction with FIG. 5 and FIG. 6. Internal wall 40 of retaining cap 30 is furnished with opposing guide rails 60, 62. Biasing portion 46 of valve member 32 includes opposing guide slots 64, 66 which are adapted to receive guide rails 60, 62. The cooperation between guide rails 60, 62 and guide slots 64, 66 allows head portion 44 of valve member 32 to move within fluid passage 42 without becoming lodged or cocked therein. Sufficient clearance exists between guide rails 60, 62 and guide slots 64, 66 thereby allowing fluid to flow therebetween, into bypass openings 58, and through fluid passage 42. The operation of Y-site connector 26 will now be explained in conjunction with FIG. 5 and FIG. 6.

Now referring to FIG. 5 and FIG. 6, when valve member 32 is not exposed to external forces, it assumes the position depicted in FIG. 5. This position is defined as the closed position. In the closed position, outwardly extending shoulder 48 contacts sealing surface 50 of retaining cap 30 and no fluid is allowed to pass between first entrance opening 36 to exit opening 38 via fluid passage 42. This sealing relation prevents fluid back flow through passage 42 and out first entrance opening 36. When it is desired to introduce medication into first entrance opening 36, syringe 68 is used to downwardly depress 70 head portion 44 of valve member 32. Once head portion 44 has been sufficiently depressed fluid is pushed through syringe 70 and into longitudinal slot 72 of head portion 44. From longitudinal slot 72 the contents of syringe 68 are free to flow through guide slots 64, into bypass openings 58 and into fluid passage 42. Once syringe 68 is removed from first entrance opening 36, biasing portion 46 of valve member 32 urges head portion 44 upwardly thereby reestablishing the fluid-tight seal between outwardly extending shoulder 48 and sealing surface 50.

As can be seen from FIG. 5, top surface 74 of retaining cap 30 and top surface 76 of head portion 44 are designed for easy cleaning and do not promote fluid pooling. This design greatly reduces the possibility of bacteria being introduced into a patient's bloodstream when Y-site connector 26 undergoes multiple uses to deliver various medications.

It is important to note that Y-site connector 26 of the present invention anticipates use with many types of standard medical connectors. For example, as seen in FIG. 2, the portions of Y-site connector 26 surrounding openings 38, 52 are adapted to frictionally engage an inner surface of a standard medical tube. Retaining cap 30 can be designed to accept any number of standard medical connectors such as a male or female luer lock connector or the like.

Another important aspect of the present invention is the design feature whereby biasing portion 46 is composed of the same material used in constructing head portion 44. This design approach allows a reduction in the number of parts used to construct the Y-site connector of the present invention. Additionally, by constructing biasing portion 46 of material which will not chemically react with medications, biasing portion 46 can reside within fluid passage 42 thereby eliminating the need for elaborate sealing between fluid passage 42 and biasing portion 46. By designing biasing portion 46 from material which can be placed in direct contact with the flow of medication, the Y connector of the present invention offers distinct advantages to other prior art systems in that it is less expensive to manufacture, it accommodates less critical in design tolerances, and it can be used with prepackaged medications (this feature will be discussed in conjunction with FIG. 11).

Now referring to FIGS. 7, 8, 9, and 10, retaining cap 30 includes opposing guide rails 60, 62 which are integrally formed in internal wall 40. As was discussed above internal side walls 60, 62 act to guide the movement of valve member 32 as it travels within fluid passage 42 thereby preventing valve member 32 from cocking or otherwise becoming improperly oriented within fluid passage 42.

Valve member 32 is preferably fabricated from rubber, or any similar material which will not react to medication. Bypass openings 58 are preferably rectangular in cross-section and must be made sufficiently large such that they are not totally collapsed when depressed by syringe 68.

Now referring to FIGS. 9, 10, and 11, an important aspect of the present invention is its ability to be used both without a needle (such as shown in FIG. 6 being used with a conventional syringe) or with a needle. FIG. 11 depicts how Y-site connector 26 is used with a hypodermic needle 78. Because central portion 80 of head 44 is composed of solid resilient material, it functions as a conventional stopper (such as a latex septum or latex plug found in conventional Y-sites). To use valve member 32 with a hypodermic needle 78, needle 78 is simply inserted through head portion 44 of Y-site connector 26 until it enters hollow core 82 area of biasing portion 46. Once hypodermic needle 78 is so placed, the contents of the syringe are emptied into fluid passage 42. Upon removal of hypodermic needle 78 from head 44, head 44 is composed of material sufficiently resilient to seal the puncture made by hypodermic needle 78 thereby reducing the risk of bacterial contamination migrating into the internal surfaces of Y-site connector 26. It is important to note that the ability of the Y-site connector of the present invention to be used both as shown in FIG. 6 and as shown in FIG. 11 is primarily attributable to biasing portion 46 residing within fluid passage 42. Thus, it is easy to understand that if biasing portion 46 were remote or sealed off from fluid passage 42, the use of hypodermic needle 78 as depicted in FIG. 11 would be impossible.

Now referring to FIG. 12, in an alternative embodiment to unitary valve member 32, valve member 84 includes head portion 86 and spring bias portion 88. Preferably, head portion 86 is made from a soft pliable material such as silicone, rubber or the like. Spring bias portion 88 is preferably constructed from metal and may, or may not, be bonded to valve member 84. Although valve member 84 is constructed somewhat differently from valve 32 (see FIG. 9), they function identically.

The foregoing detailed description shows that the preferred embodiments of the present invention are well suited to fulfill the objects of the invention. It is recognized that those skilled in the art may make various modifications or additions to the preferred embodiments chosen here to illustrate the present invention, without departing from the spirit of the present invention. For example, it is contemplated that the Y-site connector of the present invention can be modified to interface to any number of standard medical-type connectors. Also, it is contemplated that the connector of the present invention can be constructed from any wide range of materials which are not reactive to chemicals found in medications, body fluids, or the like. Accordingly, it is to be understood that the subject matter sought to be afforded protection hereby should be deemed to extend to the subject matter defined in the appended claims, including all fair equivalents thereof.

I claim:

1. A medical valve assembly having a puncturable valve comprising:

a valve body having first and second openings and a first internal wall joining said first and second openings, said first internal wall forming a first fluid passage for communicating a first fluid between said first and second opening, said first internal wall including a seating surface; and a valve member disposed in and movable within said first fluid passage and adapted to contact said seating surface thereby preventing said first fluid from communicating between said first and second openings through said first fluid passage, wherein said valve member is fabricated from puncturable material;

whereby, when a force of sufficient urging is exerted against said valve member, said valve member is displaced from said seating surfacing thereby permitting said first fluid to communicate between said first and second openings through said first fluid passage, said communication of said first fluid through said first fluid passage also being accomplished by inserting a hypodermic needle through said puncturable valve member, and into said first fluid passage and dispensing said first fluid from said hypodermic needle into said first fluid passage;

urging means disposed in said first fluid passage for urging said valve member against said seating surface;

said valve member and said urging means integrally formed as one piece, said urging means being a membrane concentrically pleated to form an elastic structure which regains its original shape after it has been compressed; and said valve body further comprises a third opening and a second internal wall, said second internal wall joining said third opening to said first fluid passage, said second internal wall forming a second fluid passage for communicating a second fluid between said third opening and said first fluid passage.

2. The valve assembly of claim 1, wherein said urging means includes a metallic spring.

3. The valve assembly of claim 1, further including means for aligning said urging means within said first fluid passage.

4. The valve assembly of claim 3, wherein said aligning means includes an alignment rail disposed on said internal wall of said first fluid passage and an alignment slot disposed in said urging means, whereby said alignment rail and alignment slot are adapted to cooperatively engage thereby guiding said valve member and maintaining said valve member in a fixed orientation within said first fluid passage.

5. The valve assembly of claim 4, wherein said cooperative engagement between said alignment rail and said alignment slot is sufficiently free to allow said fluid to pass between said alignment rail and said alignment slot.

6. The valve assembly of claim 1, wherein said urging means includes a generally tubular body having a central cavity forming a passage for said first fluid as it travels from said first opening to said second opening.

7. The valve assembly of claim 6, wherein said tubular body of said urging means includes side walls surrounding said central cavity wherein said side walls include holes communicating through said side walls thereby connecting said central cavity of said tubular body to an exterior surface of said tubular body.

8. A normally closed medical valve and tubing connector assembly for introducing and removing fluids from a patient comprising:
a retaining cap having a fluid passage means for conveying fluid through said retaining cap, said retaining cap including first and second openings connected by a first internal wall and alignment rails integral with said first internal wall, and
a valve member dimensioned to fit within said retaining cap, said valve member comprising a head portion dimensioned to sealingly contact but reciprocate within said first entrance opening and a biasing portion dimensioned to sealingly contact but reciprocate within said internal wall, said valve member including a longitudinal slot through said head portion and opposing guide slots running the length of said biasing portion which align said valve member within said retaining cap by engaging said alignment rails of said retaining cap, and
wherein said biasing portion is integral with said head portion, and said valve member is biased within said retaining cap into a position normally closed against ingress fluid flow, and
wherein said biasing portion is a membrane concentrically pleated to form an elastic structure which regains its original shape after being compressed, and
wherein said valve member is aligned within said retaining cap through mating of said alignment rails of said retaining cap into said guide slots, said guide slots being of larger dimension than said alignment rails of said retaining cap creating a flow-through path for fluid transmission between said alignment rails of said retaining cap and said guide slots,
whereby said valve member is actuated by inserting a male connector into said first entrance opening depressing said head portion to allow fluid communication through said retaining cap along a path originating at said first entrance opening through said longitudinal slot, said path extending along said guide slots and terminating at the far end of said internal wall, fluid communication being interruptable by removing the cannula from said first entrance opening which results in the return of said head portion to its normally closed position, and
said valve body further comprises a third opening and a second internal wall, said second internal wall joining said third opening to said first fluid passage, said second internal wall forming a second fluid passage for communicating a second fluid between said third opening and said first fluid passage.

* * * * *